United States Patent
Suhr

(10) Patent No.: US 6,761,734 B2
(45) Date of Patent: Jul. 13, 2004

(54) SEGMENTED BALLOON CATHETER FOR STENTING BIFURCATION LESIONS

(76) Inventor: William S. Suhr, 14 Shoreside Dr., South Barrington, IL (US) 60010

(*) Notice: Subject to any disclaimer, the term of this patent is extended or adjusted under 35 U.S.C. 154(b) by 0 days.

(21) Appl. No.: 10/201,755

(22) Filed: Jul. 22, 2002

(65) Prior Publication Data
US 2004/0015231 A1 Jan. 22, 2004

(51) Int. Cl.$^7$ .................................................. A61F 2/06
(52) U.S. Cl. ..................................................... 623/1.35
(58) Field of Search ............................. 623/1.35, 1.11; 606/192, 194, 198, 195

(56) References Cited

U.S. PATENT DOCUMENTS

| | | | |
|---|---|---|---|
| 5,226,889 A | 7/1993 | Sheiban | |
| 5,395,333 A | 3/1995 | Brill | |
| 5,415,635 A | 5/1995 | Bagaoisan et al. | |
| 5,669,924 A | 9/1997 | Shaknovich | |
| 5,697,967 A | 12/1997 | Dinh et al. | |
| 5,788,708 A | 8/1998 | Hegde et al. | |
| 5,820,595 A | 10/1998 | Parodi | |
| 5,855,565 A | 1/1999 | Bar-Cohen et al. | |
| 6,013,085 A | 1/2000 | Howard | |
| 6,048,350 A | 4/2000 | Vrba | |
| 6,048,361 A | 4/2000 | Von Oepen | |
| 6,056,775 A | 5/2000 | Borghi et al. | |
| 6,099,497 A | 8/2000 | Adams et al. | |
| 6,129,738 A | 10/2000 | Lashinski et al. | |
| 6,156,005 A | 12/2000 | Theron | |
| 6,187,034 B1 | 2/2001 | Frantzen | |
| 6,206,915 B1 | 3/2001 | Fagan et al. | |
| 6,210,429 B1 | 4/2001 | Vardi et al. | |
| 6,264,682 B1 | 7/2001 | Wilson et al. | |
| 6,346,089 B1 * | 2/2002 | Dibie ........................ | 623/1.15 |
| 6,358,556 B1 | 3/2002 | Ding et al. | |
| 6,387,124 B1 | 5/2002 | Buscemi et al. | |
| 6,494,905 B1 * | 12/2002 | Zedler et al. .............. | 623/1.15 |

OTHER PUBLICATIONS

Topol, Eric J., Textbook of Interventional Cardiology (3rd Edition, 1999), pp. 434 and 687.

* cited by examiner

Primary Examiner—Kevin T. Truong
(74) Attorney, Agent, or Firm—Henry C. Query, Jr.

(57) ABSTRACT

A segmented balloon catheter for use in treating a condition of a blood vessel occurring near a bifurcation comprises a shaft which includes a proximal end, a distal end and a longitudinal passageway that extends therethrough from the proximal end to the distal end. A first balloon portion is mounted on the shaft adjacent the distal end, and a second balloon portion is mounted on the shaft adjacent the first balloon portion. The shaft also comprises a transverse port which extends between the longitudinal passageway and the exterior of the segmented balloon catheter from between the first and second balloon portions. In this manner, a proximal end of a first guide wire which is pre-positioned in the main vessel may be inserted into the distal end of the shaft and threaded through the longitudinal passageway and out the proximal end of the shaft, and a proximal end of a second guide wire which is pre-positioned in the side branch vessel may be inserted into the transverse port and threaded through the longitudinal passageway and out the proximal end of the shaft.

35 Claims, 4 Drawing Sheets

SEGMENTED BALLOON CATHETER FOR STENTING BIFURCATION LESIONS

BACKGROUND OF THE INVENTION

The present invention relates to a balloon catheter which may be used to deliver and deploy a stent in a blood vessel. More particularly, the invention relates to a segmented balloon catheter which may be used to deploy one or more stents in a bifurcation of the blood vessel in order to treat an occlusion or lesion occurring in or near the bifurcation.

Balloon catheters are commonly used to treat certain conditions of a blood vessel, such as a partial or total occlusion or lesion of the vessel which may be caused by, for example, atherosclerotic plagues or thrombosis. In an angioplasty procedure, the balloon portion of the catheter is advanced over a guide wire to the site of the occlusion and inflated to compress the occlusion and thereby restore normal blood flow through the vessel. In some instances, a stent may be implanted in the blood vessel to prevent the occlusion from recurring. A balloon catheter is commonly used to deliver and deploy the stent in such a stenting or stent implantation procedure. The stent is typically mounted in its unexpanded state on the balloon portion of the catheter, delivered to the site of the occlusion and then deployed or implanted in the vessel by inflating the balloon portion.

Prior art stenting procedures often are unsuitable for treating a condition of a blood vessel occurring at or near a bifurcation of the blood vessel, that is, the intersection of a main vessel with a side branch vessel. One method for stenting an occlusion in a bifurcation involves implanting a first stent in the main vessel adjacent the bifurcation and then implanting a second stent in the side branch vessel adjacent the bifurcation (the so-called "T-stenting" procedure). However, this requires that the guide wire for the balloon catheter which is used to deliver the second stent be threaded through the struts of the first stent and into the side branch vessel. This process can be quite difficult and time consuming. Furthermore, the stenting of the main vessel may shift plagues and thereby close off the side branch vessel, making it extremely difficult to insert the guide wire into the side branch vessel.

Also, prior to stenting, the occlusion is commonly pre-dilated using a balloon angioplasty procedure. In preparation for a balloon angioplasty procedure in a bifurcation, a first guide wire is inserted into the main vessel and a second guide wire is inserted into the side branch vessel. Thus, even if shifting plagues should close off the side branch vessel during dilation of the main vessel, the side branch vessel can still be approached via the second guide wire. However, in prior art stenting procedures for occlusions in bifurcations, the second guide wire must usually be withdrawn from the side branch vessel prior to stenting the main vessel so that it will not interfere with the deployment of the stent in the main vessel. Consequently, difficulty may be experienced in inserting the second guide wire back into the side branch vessel prior to stenting or otherwise re-treating the side branch vessel.

SUMMARY OF THE INVENTION

In accordance with the present invention, these and other disadvantages in the prior art are addressed by providing a segmented balloon catheter for use in treating a condition of a vessel occurring near a bifurcation that is defined by the intersection of a main vessel with a side branch vessel. The segmented balloon catheter comprises a shaft which includes a proximal end, a distal end and a longitudinal passageway that extends therethrough from the proximal end to the distal end; a first balloon portion which is mounted on the shaft adjacent the distal end; and a second balloon portion which is mounted on the shaft adjacent the first balloon portion. The shaft also comprises a transverse port which extends between the longitudinal passageway and the exterior of the segmented balloon catheter from between the first and second balloon portions. A proximal end of a first guide wire which is pre-positioned in the main vessel may be inserted into the distal end of the shaft and threaded through the longitudinal passageway and out the proximal end of the shaft. In addition, a proximal end of a second guide wire which is pre-positioned in the side branch vessel may be inserted into the transverse port and threaded through the longitudinal passageway and out the proximal end of the shaft. In this manner, the first and second balloon portions may be guided to the bifurcation on the first and second guide wires.

In accordance with one embodiment of the invention, the segmented balloon catheter also comprises a stent which is mounted on the first and second balloon portions. In addition, the stent may comprise a window which is aligned with the transverse port in the shaft and through which the second guide wire extends. In this manner, the segmented balloon catheter may be used to deliver and deploy the stent in the main vessel adjacent the bifurcation. Furthermore, a second balloon catheter may then be threaded onto the second guide wire and used to deliver a second stent through the window and into the side branch vessel adjacent the bifurcation.

Thus, the segmented balloon catheter of the present invention provides a simple and efficient means for treating a condition of a blood vessel occurring at or near a bifurcation of the blood vessel. Since the segmented balloon catheter requires the pre-positioning of the first and second guide wires in the main and side branch vessels, respectively, the second guide wire can remain in place in the side branch vessel after a pre-dilation procedure, thereby eliminating the need to withdraw the second guide wire prior to stenting the main vessel. Also, since the second guide wire is threaded through the lateral port between the first and second balloon portions, the second guide wire will guide the placement of the first and second balloon portions across the opening to the side branch vessel. In addition, because the second guide wire is threaded through the stent before the stent is introduced into the vessel, the second guide wire may remain in position while the stent is deployed in the main vessel, thereby eliminating the need to thread the second guide wire through the stent after the stent is deployed in the main vessel. Furthermore, since a second stent may be deployed in the side branch vessel on the second guide wire, the first guide wire may remain in the main vessel during the stenting of the side branch vessel in the event the main vessel requires a subsequent treatment.

These and other objects and advantages of the present invention will be made apparent from the following detailed description, with reference to the accompanying drawings. In the drawings, the same reference numbers are used to denote similar elements in the various embodiments.

DETAILED DESCRIPTION OF THE PREFERRED EMBODIMENTS

The present invention is directed to a balloon catheter which is particularly useful in delivering and deploying a stent at or adjacent a bifurcation in a blood vessel. The invention may be used with any conventional balloon catheter delivery system, including the over-the-wire balloon system or the rapid exchange balloon system. In addition, the invention may be used to deploy any conventional balloon-deployable stent. Therefore, the scope of the present invention should not be limited to the exemplary delivery system and stents discussed below.

Figure 1:
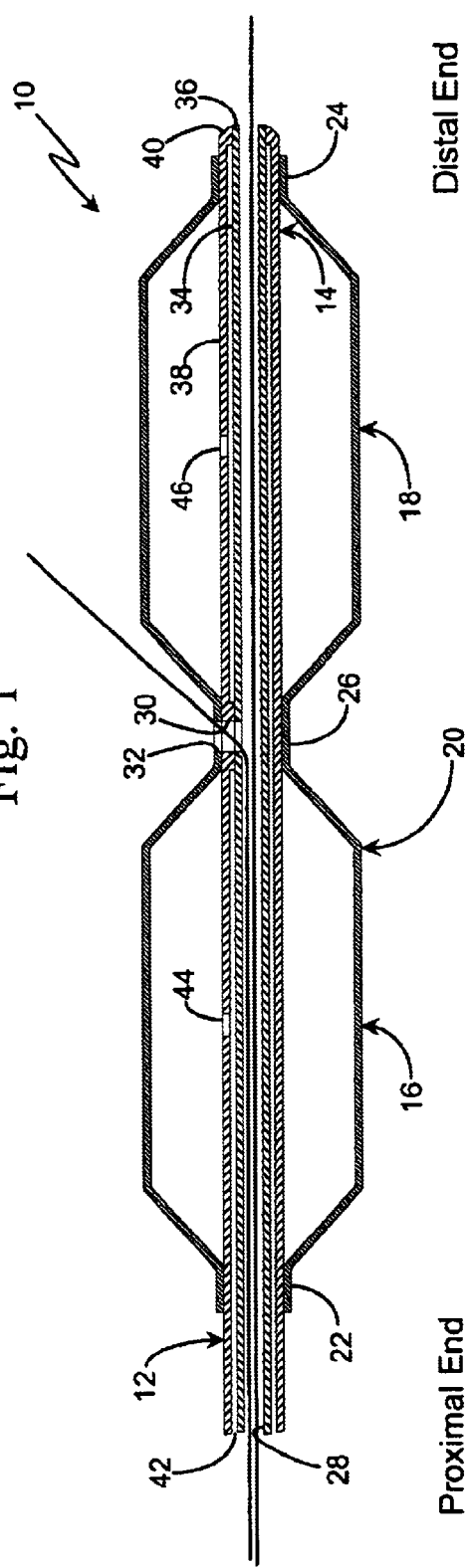
FIG. 1 is a longitudinal cross sectional view of the segmented balloon catheter of the present invention shown in its inflated condition.

Referring to FIG. 1, the segmented balloon catheter of the present invention, which is indicated generally by reference number 10, is shown to comprise an elongated shaft 12 which includes a distal end 14 and a proximal end (not shown), a first cylindrical balloon portion 16 which is mounted on the distal end, and a second cylindrical balloon portion 18 which is mounted on the distal end adjacent the first balloon portion. Each balloon portion 16, 18 is made of a conventional material, such as a polyolefin copolymer, and is secured and sealed to the shaft 12 by suitable means, such as via heat bonding or an appropriate adhesive. More preferably, the first and second balloon portions 16, 18 comprise separate portions of a single balloon head 20 which comprises a proximal end 22, a distal end 24 and a midpoint 26 which lies between the first and second balloon portions. Moreover, the balloon head 20 is ideally secured and sealed to the shaft 12 at its proximal and distal ends 22, 24, and preferably also at its midpoint 26.

The shaft 12 comprises a longitudinal passageway 28 that extends axially therethrough between the distal end 14 and the proximal end. The shaft 12 also includes a transverse port 30 that extends between the longitudinal passageway 28 and a corresponding hole 32 which is formed in the balloon head 20 between the first and second balloon portions 16, 18. The shaft 12 may be made of any suitable material, such as polyethylene.

In the embodiment of the invention shown in FIG. 1, the shaft 12 comprises an inner tube 34 which has a distal end 36 and an outer tube 38 which has a distal end 40, and the inner and outer tubes are secured and sealed together at their distal ends to define an inflation passageway 42 between the inner and outer tubes that is separated from the longitudinal passageway 28. Furthermore, the inflation passageway 42 communicates with the interior of each of the first and second balloon portions 16, 18 via respective first and second inflation holes 44, 46 which extend transversely through the outer tube 38. In this manner, an inflation fluid from an inflation device (not shown) may be communicated through the inflation passageway 42 to inflate the first and second balloon portions 16, 18. As shown in FIG. 1, the balloon head 20 is ideally sealed to the outer tube 38 around the hole 32, and the outer tube is sealed to the inner tube 34 around the transverse port 30, so that the inflation fluid will not exit the inflation passageway 42 through either the hole or the port.

Figure 2:
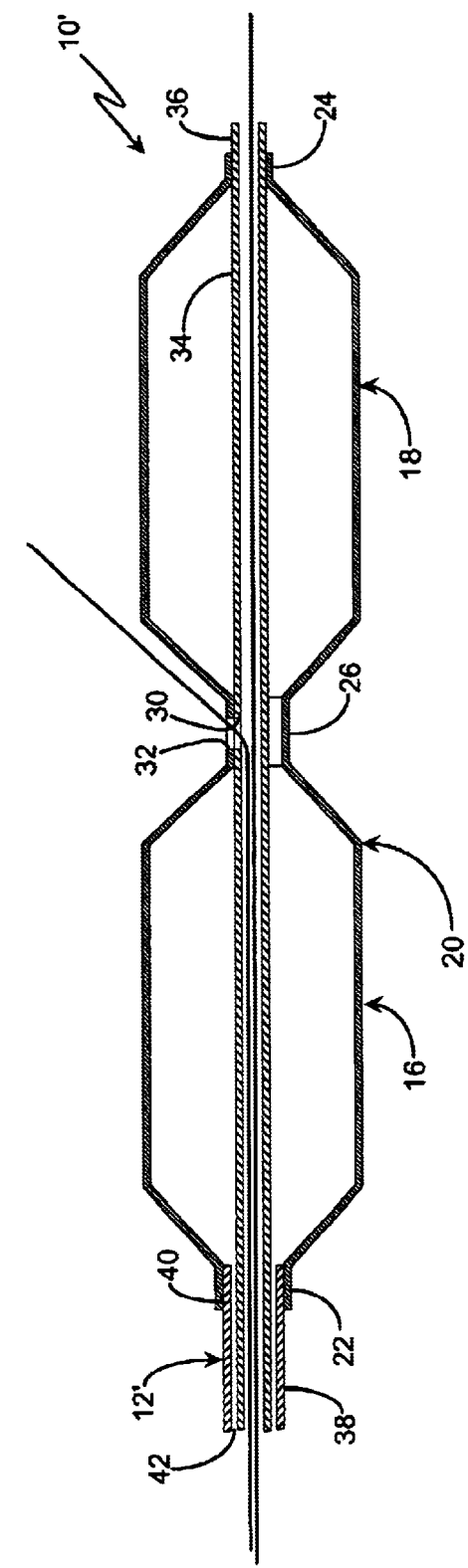
FIG. 2 is a longitudinal cross sectional view of a second embodiment of the segmented balloon catheter of the present invention shown in its inflated condition.

In an alternative embodiment of the invention which is shown in FIG. 2, the segmented balloon catheter, which is indicated generally by reference number 10', is shown to comprise a balloon head 20 that is secured to the distal end 14 of a modified shaft 12'. As in the previous embodiment, the balloon head 20 includes a first balloon portion 16, a second balloon portion 18, a proximal end 22, a distal end 24 and a midpoint 26 which lies between the first and second balloon portions. In addition, the shaft 12' includes an inner tube 34 having a distal end 36 and an outer tube 38 having a distal end 40. However, in this embodiment the distal end 36 of the inner tube 34 is spaced axially from the distal end 40 of the outer tube 38. Furthermore, the proximal end 22 of the balloon head 20 is secured and sealed to the distal end 40 of the outer tube 38, and the distal end 24 of the balloon head is secured and sealed to the distal end 36 of the inner tube 34. In addition, the midpoint 26 of the balloon head 20 ideally comprises an inner diameter which is greater than the outer diameter of the inner tube 34. In this manner, fluid from the inflation device (not shown) may be communicated to the first and second balloon portions 16, 18 directly via the inflation passageway 42 that is formed between the inner and outer tubes 34, 38 of the shaft 12'. In addition, the balloon head 20 is ideally sealed to the inner tube 34 around the hole 32 to prevent the inflation fluid from exiting the balloon head through the hole.

In an alternative to the present invention which is not illustrated in the drawings, the segmented balloon catheter 10, 10' could comprise a separate inflation lumen which is connected between the inflation device and each of the first and second balloon portions 16, 18. Such an inflation lumen could be positioned within or radially outside of the shaft 12, 12'. The construction and operation of such an alternative will be readily apparent to the person of ordinary skill in the art.

Figure 3:
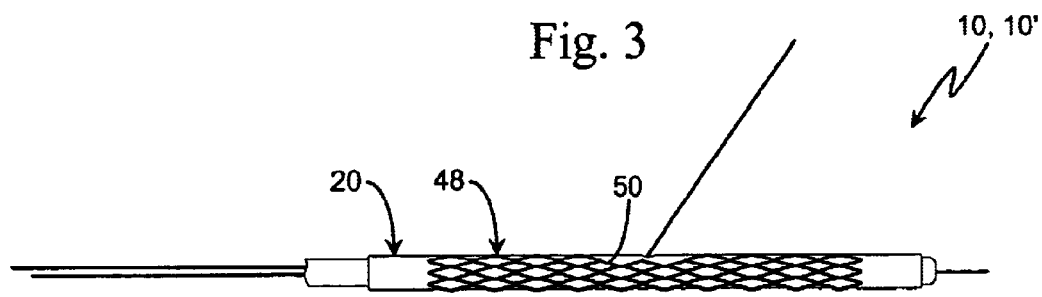
FIG. 3 is a front elevation view of the segmented balloon catheter of the present invention shown in its un-inflated condition.

Referring now to FIG. 3, the segmented balloon catheter 10, 10' of the present invention may be used to deliver and deploy a stent 48 in a blood vessel (not shown). The stent 48 may be any conventional balloon expandable stent which is used to treat a condition of a blood vessel, such as an occlusion or lesion that is caused by, for example, a stenosis or restenosis of the vessel. In one embodiment of the invention, the stent 48 is ideally a drug eluting or drug coated stent, which will help prevent restenosis following implantation of the stent. An example of a drug eluting stent and a method for making the same is disclosed in U.S. Pat. No. 6,206,915, which is hereby incorporated herein by reference.

Figure 4:
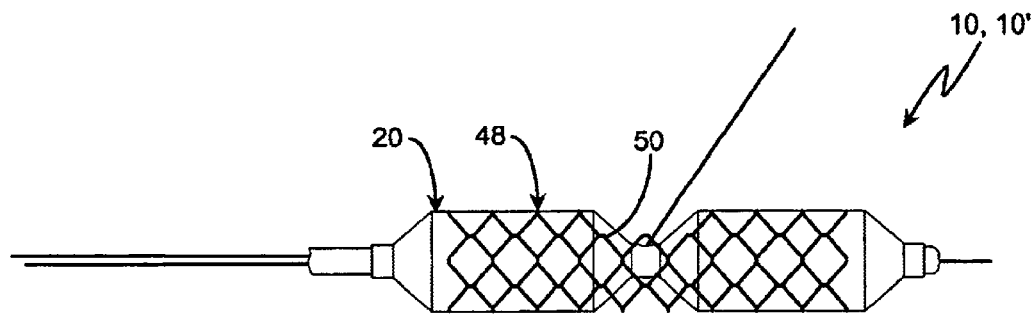
FIG. 4 is a front elevation view of the segmented balloon catheter of FIG. 2 shown in its inflated condition.

The stent 48 is removably mounted on the balloon head 20 of the segmented balloon catheter 10, 10'. Furthermore, for reasons which will be made apparent below, the stent 48 preferably comprises an enlarged cell or window 50 which is aligned with the hole 32 in the balloon head 20. In its unexpanded condition shown in FIG. 3, the stent 48 comprises a diameter which is approximately the same as or slightly larger than the diameter of the uninflated first and second balloon portions 16, 18. When the first and second balloon portions 16, 18 are inflated, the stent 48 will expand into its expanded or deployed condition shown in FIG. 4.

Figure 5:
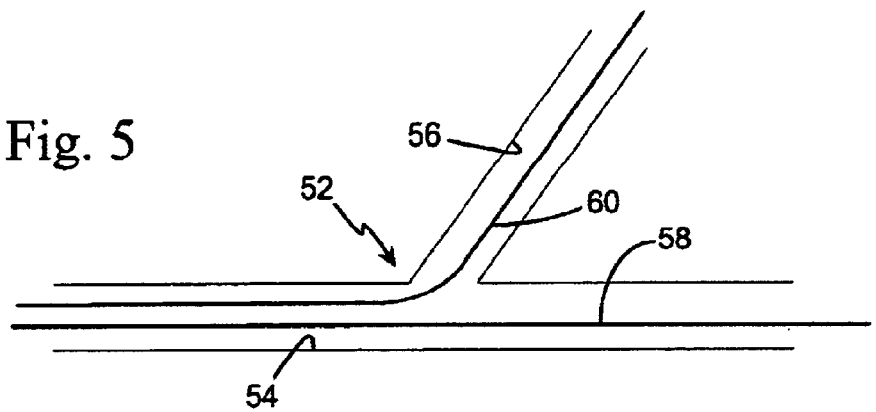
FIG. 5 is a schematic representation of an exemplary bifurcation in a blood vessel.

The segmented balloon catheter 10, 10' of the present invention is particularly useful in treating an occlusion occurring at or near a bifurcation of a blood vessel. As shown in FIG. 5, a bifurcation 52 is the site where a main vessel 54 is intersected by a side branch vessel 56. The occlusion, which may be caused by a stenosis or restenosis in the blood vessel, may be located in the main vessel 54 upstream of the side branch vessel 56, in the main vessel downstream of the side branch vessel, at the intersection of the main vessel and the side branch vessel, in the side branch vessel downstream of the main vessel, or in a combination of any of these locations. As will be made apparent below, the segmented balloon catheter 10, 10' may be used to deploy the stent 48 to treat an occlusion occurring in any of these locations.

Figure 6:
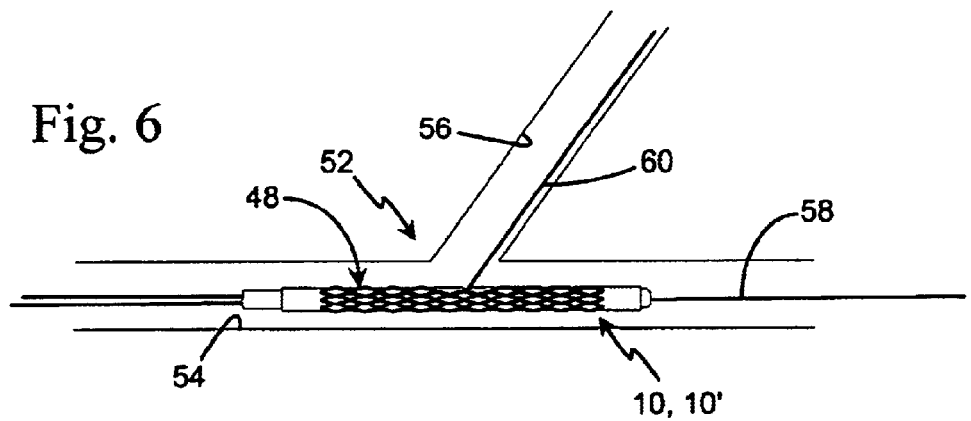
FIGS. 6 through 10 are sequential representations of the method for treating the bifurcation of FIG. 5 using the segmented balloon catheter of the present invention.

Prior to commencing the stenting procedure of the present invention, the main vessel 54 and the side branch vessel 56 may be pre-dilated in a conventional balloon angioplasty procedure. In preparation for such a pre-dilation procedure, a first conventional guide wire 58 is positioned in the main vessel 54 and a second conventional guide wire 60 is positioned in the side branch 56, as shown in FIG. 5. After the pre-dilation procedure is completed, the balloon catheter which is used in such a procedure is removed and the segmented balloon catheter 10, 10' with the stent 48 mounted thereon is threaded onto both of the guide wires 58, 60 as follows. The proximal end of the first guide wire 58 (that is, the end closest to the doctor) is inserted into the distal end 36 of the inner tube 34 and threaded through the longitudinal passageway 28 until it exits the proximal end of the shaft 12, 12'. The proximal end of the second guide wire 60 is then inserted through the window 50 in the stent 48, the hole 32 in the balloon head 20 and the transverse port 30 in the shaft 12, 12'. The second guide wire 60 is then threaded through the longitudinal passageway 28 until it exits the proximal end of the shaft 12, 12'. The balloon head 20 and stent 48 are then advanced through the main vessel 54 to the bifurcation 52, as shown in FIG. 6. Since the second guide wire 60 is threaded through the lateral port 30 between the first and second balloon portions 16, 18, the second guide wire will help position the first and second balloon portions in the main vessel 54 across the opening to the side branch vessel 56.

Figure 7:
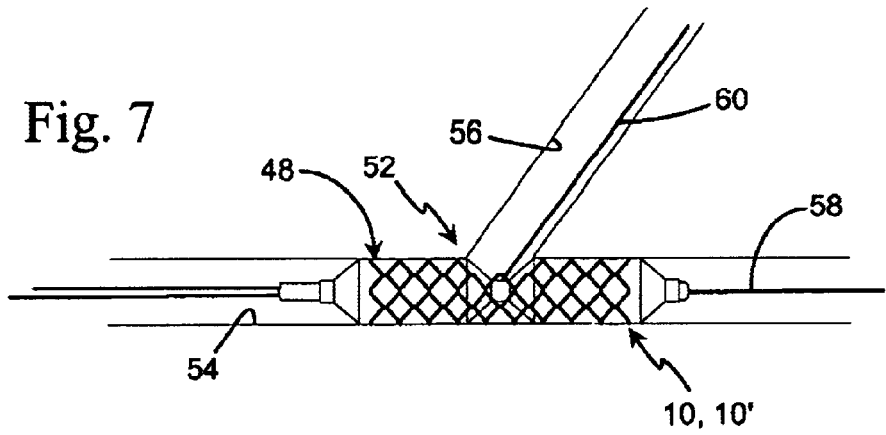
Figure 8:
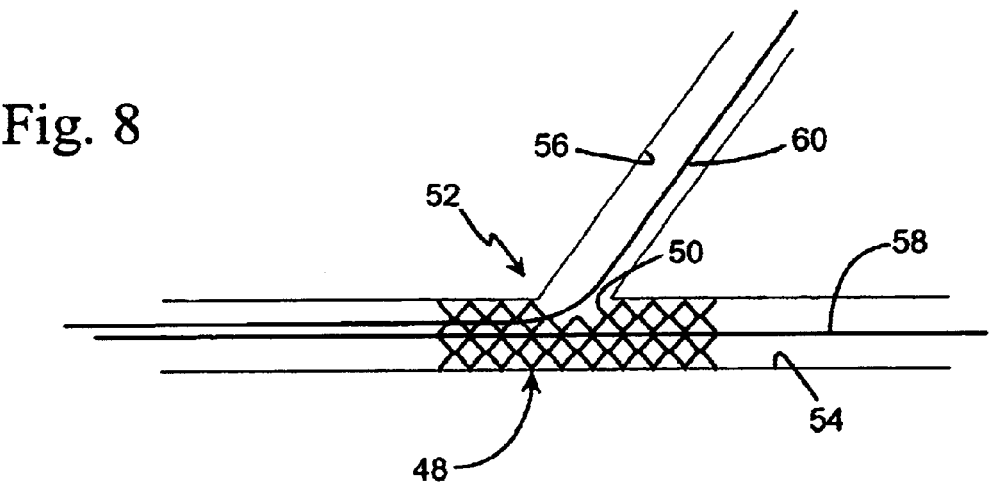

Once the stent 48 is in position at the bifurcation 52, the first and second balloon portions 16, 18 are inflated to expand the stent 48 into its deployed condition, as shown in FIG. 7. The first and second balloon portions 16, 18 are then deflated to allow the segmented balloon catheter 10, 10' to be withdrawn from the bifurcation 52 and removed from the first guide wire 58. When the stent 48 is deployed as just described, the second guide wire 60 will automatically be positioned through the window 50, as shown in FIG. 8. If necessary, the segmented balloon catheter 10, 10', or any conventional balloon catheter, can then be threaded onto the second guide wire 60, advanced partially into the side branch 56 and inflated to align the window 50 with the side branch.

Figure 9:
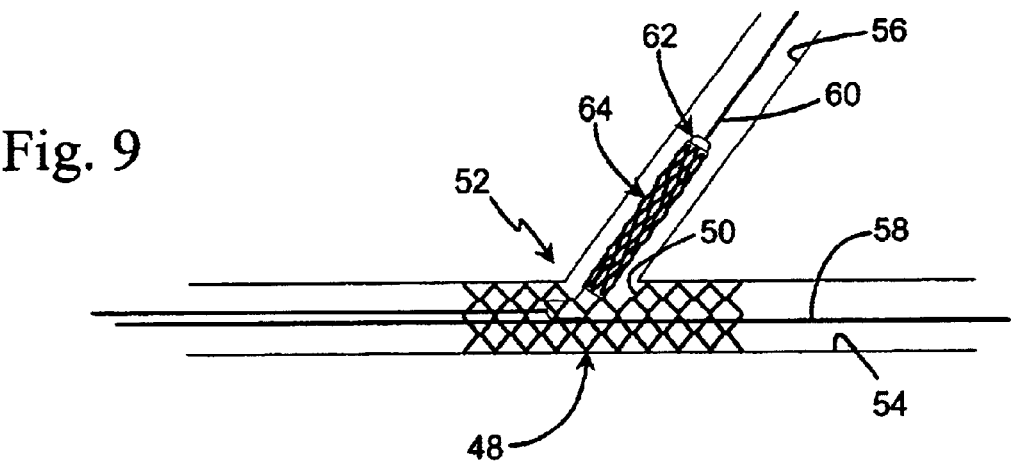
Figure 10:
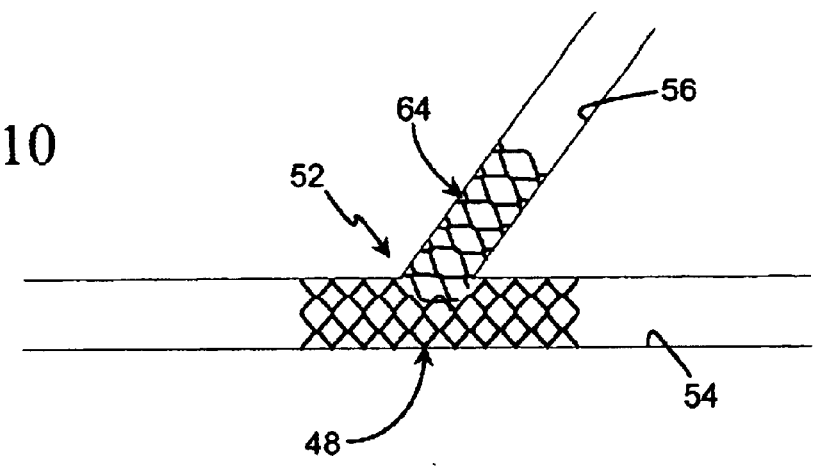

If necessary, a second stent may be implanted in the side branch 56 to treat an occlusion located at or near the bifurcation 52. Referring to FIG. 9, this may be accomplished by first threading a second balloon catheter 62 having a second stent 64 mounted thereon onto the second guide wire 60. The second balloon catheter 62 may be similar to the segmented balloon catheter 10, 10', or it may simply be any conventional balloon catheter. Similarly, the second stent 64 may be similar to the stent 48, or it may by any standard balloon expandable stent. The second balloon catheter 62 is advanced through the window 50 in the stent 48 and into the side branch 56. The second balloon catheter 62 is then inflated to expand the second stent 64 into its deployed condition in the side branch 56. The second balloon catheter 62 may then deflated and removed. As shown in FIG. 10, the second stent 64 is preferably positioned such that a portion of the stent is located at the intersection of the main and side branch vessels 54, 56. This will ensure that any occlusion which may exist at the intersection will be suitably engaged by the stents 48, 64.

It should be recognized that, while the present invention has been described in relation to the preferred embodiments thereof, those skilled in the art may develop a wide variation of structural and operational details without departing from the principles of the invention. For example, the various elements shown in the different embodiments may be combined in a manner not illustrated above. Therefore, the appended claims are to be construed to cover all equivalents falling within the true scope and spirit of the invention.

I claim:

1. A segmented balloon catheter for use in treating a condition of a vessel occurring near a bifurcation that is defined by the intersection of a main vessel with a side branch vessel, the segmented balloon catheter comprising:

a shaft which includes a proximal end, a distal end and a longitudinal passageway that extends therethrough from the proximal end to the distal end;

a first balloon portion which is mounted on the shaft adjacent the distal end;

a second balloon portion which is mounted on the shaft adjacent the first balloon portion;

the shaft comprising a transverse port which extends between the longitudinal passageway and the exterior of the segmented balloon catheter from between the first and second balloon portions;

wherein a proximal end of a first guide wire which is pre-positioned in the main vessel may be inserted into the distal end of the shaft and threaded through the longitudinal passageway and out the proximal end of the shaft; and wherein a proximal end of a second guide wire which is pre-positioned in the side branch vessel may be inserted into the transverse port and threaded through the longitudinal passageway and out the proximal end of the shaft;

whereby the first and second balloon portions may be guided to the bifurcation on the first and second guide wires.

2. The segmented balloon catheter of claim 1, wherein the first and second balloon portions comprise separate portions of a single balloon head.

3. The segmented balloon catheter of claim 2, wherein the balloon head comprises a proximal end, a distal end and a midpoint which is located between the first and second balloon portions.

4. The segmented balloon catheter of claim 3, wherein the proximal and distal ends of the balloon head are each secured and sealed to the shaft.

5. The segmented balloon catheter of claim 4, wherein the midpoint of the balloon head is secured and sealed to the shaft.

6. The segmented balloon catheter of claim 2, wherein the balloon head comprises a hole which is aligned with the transverse port in the shaft.

7. The segmented balloon catheter of claim 1, wherein the shaft comprises an inner tube which comprises a first distal end and an outer tube which comprises a second distal end.

8. The segmented balloon catheter of claim 7, wherein the first and second distal ends are secured and sealed together to form an inflation passageway between the inner and outer tubes.

9. The segmented balloon catheter of claim 8, wherein the outer tube comprises a first inflation hole which extends between the inflation passageway and the first balloon portion and a second inflation hole which extends between the inflation passageway and the second balloon portion.

10. The segmented balloon catheter of claim 7, wherein:
the first and second balloon portions comprise separate portions of a single balloon head which comprises a proximal end, a distal end and a midpoint that is located between the first and second balloon portions;
the distal end of the balloon head is secured and sealed to the first distal end of the inner tube; and
the proximal end of the balloon head is secured and sealed to the second distal end of the outer tube.

11. The segmented balloon catheter of claim 10, wherein an inflation passageway is defined between the inner and outer tubes.

12. The segmented balloon catheter of claim 11, wherein the midpoint comprises an inner diameter which is larger than the outer diameter of the inner tube.

13. The segmented balloon catheter of claim 1, further comprising a stent which is mounted on the first and second balloon portions.

14. The segmented balloon catheter of claim 13, wherein the stent comprises a window which is aligned with the transverse port in the shaft.

15. The segmented balloon catheter of claim 14, wherein the stent is a drug coated or drug eluting stent.

16. A method for treating a condition of a vessel occurring near a bifurcation that is defined by the intersection of a main vessel with a side branch vessel, the method comprising:
pre-positioning a first guide wire in the main vessel and a second guide wire in the side branch vessel;
providing a first balloon catheter having distal end, a proximal end, a longitudinal passageway extending therethrough from the distal end to the proximal end, a first balloon portion, a second balloon portion and a lateral port extending between the longitudinal passageway and the exterior of the balloon catheter from between the first and second balloon portions;
mounting a first expandable stent over the first and second balloon portions;
threading a proximal end of the first guide wire into the distal end of the first balloon catheter and out the proximal end of the first balloon catheter;
threading a proximal end of the second guide wire through the first stent, into the lateral port and out the proximal end of the first balloon catheter;
advancing the first and second balloon portions into the main vessel adjacent the bifurcation; and
inflating the first and second balloon portions to thereby implant the first stent in the main vessel adjacent the bifurcation.

17. The method of claim 16, further comprising:
providing a second balloon catheter having a longitudinal passageway extending therethrough and a balloon portion;
mounting a second expandable stent over the balloon portion of the second balloon catheter;
threading the proximal end of the second guide wire through the longitudinal passageway of the second balloon catheter;
advancing the balloon portion of the second balloon catheter through the first stent and into the side branch vessel adjacent the bifurcation; and
inflating the balloon portion of the second balloon catheter to thereby implant the second stent in the side branch vessel adjacent the bifurcation.

18. The method of claim 17, further comprising the following preliminary steps:
providing a third balloon catheter having a longitudinal passageway extending therethrough and a balloon portion;
threading the proximal end of the second guide wire through the longitudinal passageway of the third balloon catheter;
advancing the balloon portion of the third balloon catheter at least partially through a window in the first stent and into the side branch vessel; and
inflating the balloon portion of the third balloon catheter to thereby align the window with the side branch vessel.

19. The method of claim 16, further comprising providing a therapeutic substance on the first stent.

20. The method of claim 19, wherein the first stent is a drug coated or drug eluting stent.

21. A segmented balloon catheter for treating a bifurcation of a vessel which is defined by the intersection of a main vessel with a side branch vessel, the segmented balloon catheter comprising:
an elongated shaft which includes a distal end;
a first balloon portion which is disposed on the shaft adjacent the distal end;
a second balloon portion which is disposed on the shaft adjacent the first balloon portion;
the shaft comprising a transverse port which is positioned between the first and second balloon portions;
wherein in use a proximal end of a first guide wire which is pre-positioned in the main vessel is inserted into the distal end of the shaft and a proximal end of a second guide wire which is pre-positioned in the side branch vessel is inserted into the transverse port; and
wherein the first and second balloon portions are guided to the bifurcation by advancing the catheter through the main vessel on the first and second guide wires.

22. The segmented balloon catheter of claim 21, wherein at least a distal end of the first balloon portion and a proximal end of the second balloon portion are attached to the shaft.

23. The segmented balloon catheter of claim 22, wherein the shaft comprises a first elongated tube which is disposed within a second elongated tube.

24. The segmented balloon catheter of claim 23, wherein a distal end of the first tube is sealed to a distal end of the second tube to form an inflation passageway within the shaft.

25. The segmented balloon catheter of claim 23, wherein the distal end of the first balloon portion is attached to a distal end of the first tube and the proximal end of the second balloon portion is attached to a distal end of the second tube.

26. The segmented balloon catheter of claim 21, further comprising a stent which is mounted on the first and second balloon portions.

27. The segmented balloon catheter of claim 26, wherein the stent is a drug coated or drug eluting stent.

28. A method for treating a bifurcation of a vessel which is defined by the intersection of a main vessel with a side branch vessel, the method comprising:
pre-positioning a first guide wire in the main vessel and a second guide wire in the side branch vessel;
providing a first balloon catheter having a shaft, first and second balloon portions which are supported on the shaft, and a transverse port which is located between the first and second balloon portions;

mounting a first expandable stent over the first and second balloon portions;

inserting a proximal end of the first guide wire into a distal end of the shaft;

inserting a proximal end of the second guide wire through the first stent and into the port;

advancing the first balloon catheter over the first and second guide wires to position the first and second balloon portions in the main vessel adjacent the bifurcation; and inflating at least one of the first and second balloon portions to thereby implant the first stent in the main vessel adjacent the bifurcation.

29. The method of claim 28, further comprising:

withdrawing the first and second balloon portions from the bifurcation; and removing the first balloon catheter from at least the second guide wire.

30. The method of claim 29, further comprising:

providing a second balloon catheter having a shaft and a balloon portion which is supported on the shaft;

mounting a second expandable stent over the balloon portion of the second balloon catheter;

inserting the proximal end of the second guide wire into a distal end of the shaft of the second balloon catheter;

advancing the second balloon catheter over the second guide wire to insert the balloon portion of the second balloon catheter through the first stent and into the side branch vessel; and inflating the balloon portion of the second balloon catheter to thereby implant the second stent in the side branch vessel.

31. The method of claim 30, further comprising the following preliminary steps:

providing a third balloon catheter having a shaft and a balloon portion which is supported on the shaft;

inserting the proximal end of the second guide wire into a distal end of the shaft of the third balloon catheter;

advancing the third balloon catheter over the second guide wire to position the balloon portion of the third balloon catheter at least partially through a window in the first stent and into the side branch vessel; and inflating the balloon portion of the third balloon catheter to thereby force the window into alignment with the side branch vessel.

32. The method of claim 28, wherein the first stent is a drug coated or drug eluting stent.

33. The method of claim 30, wherein at least one of the first and second stents is a drug coated or drug eluting stent.

34. A system for treating a bifurcation of a vessel which is defined by the intersection of a main vessel with a side branch vessel, the system comprising:

a first guide wire which comprises a distal end that is pre-positioned in the main vessel;

a second guide wire which comprises a distal end that is pre-positioned in the side branch vessel;

a first balloon catheter which comprises a first shaft, first and second balloon portions which are supported on the first shaft, and a transverse port which is located between the first and second balloon portions;

a second balloon catheter which comprises a second shaft and a third balloon portion which is supported on the second shaft;

a first expandable stent which is mounted over the first and second balloon portions; and a second expandable stent which is mounted over the third balloon portion;

wherein in use a proximal end of the first guide wire is inserted into a distal end of the first shaft, a proximal end of the second guide wire is inserted through the first stent and into the port, the first balloon catheter is advanced on the first and second guide wires until the first and second balloon portions are positioned adjacent the bifurcation, and at least one of the first and second balloon portions is inflated to implant the first stent in the main vessel; and wherein after the first balloon catheter is withdrawn from at least the second guide wire, the proximal end of the second guide wire is inserted into a distal end of the second shaft, the second balloon catheter is advanced on the second guide wire until the third balloon portion is inserted through the first stent and into the side branch vessel, and the third balloon portion is inflated to implant the second stent in the side branch vessel.

35. The system of claim 34, wherein at least one of the first and second stents is a drug coated or drug eluting stent.

* * * * *